(12) United States Patent
Geraghty et al.

(10) Patent No.: US 7,709,788 B2
(45) Date of Patent: May 4, 2010

(54) CHEMICAL CALIBRATION METHOD AND SYSTEM

(75) Inventors: Edward Geraghty, Tyngsboro, MA (US); Vladimir Kekukh, Chestnut Hill, MA (US); Stephen N. Bunker, Wakefield, MA (US)

(73) Assignee: Implant Sciences Corporation, Wilmington, MA (US)

( * ) Notice: Subject to any disclaimer, the term of this patent is extended or adjusted under 35 U.S.C. 154(b) by 287 days.

(21) Appl. No.: 12/006,246

(22) Filed: Dec. 31, 2007

(65) Prior Publication Data

US 2009/0166524 A1 Jul. 2, 2009

(51) Int. Cl.
*B01D 59/44* (2006.01)

(52) U.S. Cl. .................. 250/282; 250/281; 250/283; 250/287; 250/288

(58) Field of Classification Search .................. 250/281, 250/282, 283, 287, 288
See application file for complete search history.

(56) References Cited

U.S. PATENT DOCUMENTS

| | | | |
|---|---|---|---|
| 5,723,861 A * | 3/1998 | Carnahan et al. | 250/287 |
| 6,291,821 B1 | 9/2001 | Danylewych-May et al. | |
| 6,627,444 B1 | 9/2003 | Goledzinowski et al. | |
| 6,828,795 B2 * | 12/2004 | Krasnobaev et al. | 324/464 |
| 6,861,646 B2 * | 3/2005 | Motchkine et al. | 250/288 |
| 6,870,155 B2 * | 3/2005 | Krasnobaev et al. | 250/283 |
| 6,888,128 B2 * | 5/2005 | Krasnobaev et al. | 250/281 |
| 7,098,672 B2 | 8/2006 | Belyakov et al. | |
| 7,244,288 B2 | 7/2007 | Belyakov et al. | |
| 2009/0078862 A1 * | 3/2009 | Rodier et al. | 250/282 |

FOREIGN PATENT DOCUMENTS

| | | |
|---|---|---|
| EP | 0 447 158 A2 | 9/1991 |
| WO | WO 97/38302 | 10/1997 |
| WO | WO 2007042763 A2 * | 4/2007 |

\* cited by examiner

*Primary Examiner*—David A Vanore
*Assistant Examiner*—Michael J Logie
(74) *Attorney, Agent, or Firm*—Muirhead and Saturnelli, LLC

(57) ABSTRACT

An explosive and narcotics detection system using an ion mobility spectrometer detects the presence of vapor or trace particles of target chemicals. The calibration of the spectrometer depends in part on the stability of a calibrant chemical that may be periodically injected together with sample gas into the ionization region of the spectrometer. The calibrant chemical produces a signal with a drift time that is known relative to target chemicals and may be used to calibrate the expected target chemical drift times. A new calibrant chemical, 5-nitrovanillin, is disclosed for this purpose.

21 Claims, 9 Drawing Sheets

CHEMICAL CALIBRATION METHOD AND SYSTEM

BACKGROUND OF THE INVENTION

1. Field of the Invention

This application relates to detection of explosives, and more particularly, to calibrating the ion mobility drift time scale of an ion mobility spectrometer for the detection of explosives.

2. Description of Related Art

Ion mobility spectrometers (IMS) are used for the identification of chemicals based on the time required for the chemical ion to traverse a drift space to a charge collecting surface under the influence of an electric field. The resultant drift time is dependent on the field strength, the distance traversed, the density, type, and flow vector of the gas within the drift space, and the physical characteristics of size and mass of the chemical species. In practice, usually the gas within the drift space is temperature-controlled dry air, and the drift distance, electric field strength, and electric field uniformity are fixed or controlled. This leaves ambient pressure, subtle irregularities in temperature, and ambient chemical species as the primary uncontrolled variables affecting the drift time. The physical properties of the chemical species together with that of the drift gas are combined into a single parameter known as the reduced mobility constant, usually written as $K_o$. In general, a large value of reduced mobility equates to rapid motion of an ion in an electric field. The reduced mobility is the mobility corresponding to standard conditions of temperature and pressure, 273 Kelvin and 760 mm.

In order to further compensate for subtle variations in temperature and pressure, a calibrant chemical may be introduced into the ion generating region of the system. Since this chemical is known, the expected drift time can be estimated if the ambient pressure is measured. For a system that is open to the atmosphere, it is sufficient to measure the pressure external to the ion drift region. The actual calibrant drift time may then be used to predict the observed drift times of any other desired ion species by reference to a table of the ratio of the reduced ion mobility of the calibrant to the target chemical. Relying on the assumption that the environment seen by the calibrant ion and the target ion is similar through the ion source and drift region, any imperfections, non-uniform electric fields, temperature variations, and the like are equally compensated for in the calibrant and target ion drift times, and the ratio should be a constant.

One variable that is species-dependent is the level of ambient humidity in the drift region. It is well-known that water molecules form clusters that attach metastabily to certain chemical species, thus changing their mass and cross section, and thus ion mobility in the drift region. In order to minimize this phenomenon, the air within the drift region is typically both heated in excess of 100 degrees Centigrade as well as dried using a drying agent, such as molecular sieve material.

In a system that is open to the atmosphere, the calibrant chemical is typically admitted along the same path that is employed for the external air sample entry into the ion generation region. Therefore, the calibrant encounters potentially humid external air and may be compromised in some manner by its presence.

In practice, the charge peak of the calibrant chemical is first identified in the spectrum of charge amplitude versus drift time after the calibrant has been introduced into the ion mobility spectrometer. The specific drift time is determined, and the expected drift times of target chemicals are calculated from a pre-measured table of the target chemical/calibrant ratios of reduced mobilities.

A "window" is generally provided around the expected drift times of the target chemicals because of effects related to instantaneous drift gas pressure and flow speed, metastable chemical adducts, gas concentration, as well as many other subtle effects.

A commonly employed calibrant is butylated hydroxytoluene (BHT), which is a food additive normally used for its anti-oxidant properties. This chemical is fairly sensitive to the level of ambient humidity and contamination chemicals in the environment. It is characterized by two chemical constituents in the gas phase, BHT and BHT+2O. These species have ion mobilities with almost, but not the same, value. The resultant charge peak in the ion mobility spectrum is thus the sum of two Gaussian-like peaks, which is in turn also a Gaussian-like peak. Each of the two chemical species has an ion transmission amplitude that varies independently with humidity and the presence of contamination chemicals from the environment. When the relative amplitudes of the two peaks vary, the apparent drift time of the sum of the two peaks will shift over the range between the mobility of each of the constituent species. Common contamination chemicals, including water vapor, are known that almost completely block ion formation of BHT ions. As such, its unstable ion transmission amplitude and variable drift time means that BHT is not a reliable calibrant for a system that is open to the atmosphere.

Accordingly, it would be desirable to provide a system and method using a calibrant chemical having a drift time and transmission amplitude that are only weakly affected by ambient environmental chemicals, including humidity, in order to ensure the stability of the calibration of the IMS.

SUMMARY OF THE INVENTION

In accordance with one aspect of the invention is a method for calibrating the drift time of an ion mobility spectrometer that is open to the atmosphere. The method utilizes an ion mobility spectrometer that includes an ionization region, a drift region, and a charge collecting surface. The ionization region may be pneumatically coupled to the drift region and the charge collecting surface. An electric field may be provided such that ions created in the ionization region are transported to the charge collecting surface, which may be disposed on the end of the drift region that is opposite to the ionization region.

In accordance with another aspect of the invention is a system for calibrating drift time. The system may include an ion mobility spectrometer that is open to the atmosphere, the ion mobility spectrometer including a gas ionization region with a sample gas inlet tube and sample gas outlet tube open to the atmosphere, a drift region with an inlet and outlet for a drift gas flow and pneumatically coupled to the ionization region, a charge collecting surface at the end of the drift region opposite the ionization region, and an electric field generator for providing an electric field between said ionization region and said charge collecting surface in order to transport ions in between. A temperature controlled oven in pneumatic communication with said ionization region may heat a solid phase sample of a calibrant chemical to produce a calibrant gas, wherein said calibrant chemical includes 5-nitrovanillin, also known as 4-hydroxy-3-methoxy-5-nitrobenzaldehyde, CAS number 6635-20-7. An analysis unit may determine the drift time of said calibrant chemical through said ion mobility spectrometer and determine the expected drift time of a target chemical using pre-determined ratio of the reduced mobilities of said target chemical and said calibrant chemical.

The ion mobility spectrometer further may have a sample gas inlet tube and a sample gas outlet tube pneumatically coupled to the ionization region. A pump may be provided for transporting the sample gas from the ambient environment through the sample gas inlet tube, then to the ionization region of the ion mobility spectrometer, and finally exhausted through the sample gas outlet tube. The drift region further may have an inlet and an outlet for a drift gas. A pump may be provided to make the drift gas traverse the length of the drift region.

An oven may be provided for heating a solid phase calibrant chemical to a temperature suitable to produce sufficient vapor pressure to provide a gaseous sample of calibrant for the ion mobility spectrometer, said temperature being in the range of 40 degrees Celsius and the melting point of 5-nitrovanillin. The gaseous sample outlet of the calibrant oven may be pneumatically coupled to the ionization region, either through the sample gas inlet tube or directly coupled into the ionization region. A source of carrier gas may be chosen from air that has been compressed by a pump and may be optionally dried. The carrier gas may transport the calibrant gaseous sample into the ionization region where it may be combined with a sample of gas from the ambient environment.

In an embodiment, the calibrant chemical may have a drift time in the ion mobility spectrometer that is distinct from the drift times typical of target chemicals. Further, the presence of the most common ambient contamination chemicals may have only a minor effect on the drift time and ionization efficiency of the calibrant chemical.

In another embodiment, the calibrant chemical may provide sufficient vapor pressure to produce sufficient ions in the ion mobility spectrometer for a peak in excess of 1% of the full scale amplitude of the instrument. The calibrant chemical may be chemically stable over a period of years, may be commonly available with a purity greater than 90%, may be minimally toxic, and may remain in the solid phase at the temperature that provides sufficient vapor pressure.

There are few suitable, chemicals that meet all of these requirements. In an embodiment, a calibrant chemical that may be used in connection with the system and method described here is commonly referred to as 5-nitrovanillin. The IUPAC name is 4-hydroxy-3-methoxy-5-nitrobenzaldehyde. The CAS number is 6635-20-7. The chemical formula is $C_8H_7NO_5$.

The calibrant chemical 5-nitrovanillin may be ionized either as a positive or as a negative ion. The drift time associated with 5-nitrovanillin does not interfere with any explosive or common narcotic chemical, which are the primary types of target chemicals. The drift time and charge amplitude of 5-nitrovanillin are little affected by most of the common ambient environment chemicals with the single exception of lactic acid and its oxide derivatives. The vapor pressure due to sublimation in the range of 40 degrees Celsius and the melting point of 5-nitrovanillin is sufficient to produce an ion charge in excess of 1% of the full scale amplitude of a typical ion mobility spectrometer. The chemical 5-nitrovanillin has been tested in operation over a period in excess of one year with no recognizable deterioration in the chemical. It is commercially available with a purity up to 99%, and its common usage is in dying fabrics. The material safety data sheet (MSDS) describes the toxicity as "irritating to the mucous membranes", which is considered to be low toxicity at the concentrations employed as a calibrant. The 5-nitrovanillin sublimes at temperatures below 100 degrees Celsius, and thus remains in the solid phase.

According to the system described herein, an ion mobility spectrometer that is open to the atmosphere is calibrated. The ion mobility spectrometer includes a gas ionization region with a sample gas inlet tube and sample gas outlet tube open to the atmosphere, a drift region with an inlet and outlet for a drift gas flow and pneumatically coupled to the ionization region, a charge collecting surface at the end of the drift region opposite the ionization region, and an electric field generator for providing an electric field between said ionization region and said charge collecting surface in order to transport ions in between. Calibrating includes heating a solid phase sample of a calibrant chemical to produce a calibrant gas using a temperature controlled oven in pneumatic communication with the ionization region, where the calibrant chemical includes 5-nitrovanillin, also known as 4-hydroxy-3-methoxy-5-nitrobenzaldehyde, CAS number 6635-20-7, determining the drift time of the calibrant chemical through said ion mobility spectrometer, and determining the expected drift time of a target chemical using a pre-determined ratio of the reduced mobilities of said target chemical and said calibrant chemical. The temperature-controlled oven may be operated at a temperature between 40 degrees Celsius and the melting point of 5-nitrovanillin. The calibrant gas may be injected into the ionization region using a carrier gas including at least one of pressurized ambient air and pressurized dry air. The solid phase sample of calibrant chemical may have a purity greater than 90%. The drift time may be determined based on the difference in the ion charge arrival time at the charge collecting surface and the time of either a pulsed ionization event or the opening of an electronic ion gate. The drift time may be discarded if an amplitude of calibrant chemical ion charge is less than 1% of the possible full scale detection amplitude or greater than 30% of the possible full scale detection amplitude. The drift time may be discarded if an ion charge peak corresponding to lactic acid or oxide derivatives thereof appears in the spectrum of drift time with an amplitude greater than half the amplitude of the ion charge peak corresponding to 5-nitrovanillin.

According further to the system described herein, a system calibrates drift time for an ion mobility spectrometer that is open to the atmosphere, the ion mobility spectrometer including a gas ionization region with a sample gas inlet tube and sample gas outlet tube open to the atmosphere, a drift region with an inlet and outlet for a drift gas flow and pneumatically coupled to the ionization region, a charge collecting surface at the end of the drift region opposite the ionization region, and an electric field generator for providing an electric field between said ionization region and said charge collecting surface in order to transport ions in between. The system includes a temperature controlled oven in pneumatic communication with the ionization region that heats a solid phase sample of a calibrant chemical to produce a calibrant gas, where the calibrant chemical includes 5-nitrovanillin, also known as 4-hydroxy-3-methoxy-5-nitrobenzaldehyde, CAS number 6635-20-7 and includes an analysis unit that determines the drift time of the calibrant chemical through the ion mobility spectrometer and determines the expected drift time of a target chemical using pre-determined ratio of the reduced mobilities of the target chemical and the calibrant chemical. The temperature-controlled oven may be operated at a temperature between 40 degrees Celsius and the melting point of 5-nitrovanillin. The calibrant gas may be injected into the ionization region using a carrier gas including at least one of pressurized ambient air and pressurized dry air. The solid phase sample of calibrant chemical may have a purity greater than 90%. The drift time may be determined based on the difference in the ion charge arrival time at the charge collecting surface and the time of either a pulsed ionization event or the opening of an electronic ion gate. The drift time may be discarded if the amplitude of calibrant chemical ion charge is less than 1% of the possible full scale detection amplitude or greater than 30% of the possible full scale detection amplitude. The drift time may be discarded if an ion charge peak corresponding to lactic acid or oxide derivatives thereof appears in the spectrum of drift time with an amplitude greater than half the amplitude of the ion charge peak corresponding to 5-nitrovanillin.

According further to the system described herein, calibrating drift time for an ion mobility spectrometer that is open to the atmosphere includes heating a solid phase sample of a calibrant chemical to produce a calibrant gas using a temperature controlled oven in pneumatic communication with the ionization region, wherein said calibrant chemical includes 5-nitrovanillin, determining the drift time of the calibrant chemical through the ion mobility spectrometer, and determining the expected drift time of a target chemical using a pre-determined ratio of the reduced mobilities of the target chemical and the calibrant chemical. The temperature-controlled oven may be operated at a temperature between 40 degrees Celsius and the melting point of 5-nitrovanillin. The calibrant gas may be injected into an ionization region of the ion mobility spectrometer using a carrier gas including at least one of pressurized ambient air and pressurized dry air. The solid phase sample of calibrant chemical may have a purity greater than 90%. The drift time may be determined based on the difference in the ion charge arrival time at a charge collecting surface of the ion mobility spectrometer and the time of either a pulsed ionization event or the opening of an electronic ion gate. The drift time may be discarded if an amplitude of calibrant chemical ion charge is less than 1% of a possible full scale detection amplitude or greater than 30% of the possible full scale detection amplitude. The drift time may be discarded if an ion charge peak corresponding to lactic acid or oxide derivatives thereof appears in the spectrum of drift time with an amplitude greater than half the amplitude of the ion charge peak corresponding to 5-nitrovanillin.

BRIEF DESCRIPTION OF THE DRAWINGS

Embodiments of the system and method described herein are detailed with reference to the several figures of the drawings, in which.

DETAILED DESCRIPTION OF VARIOUS EMBODIMENTS

Figure 1:
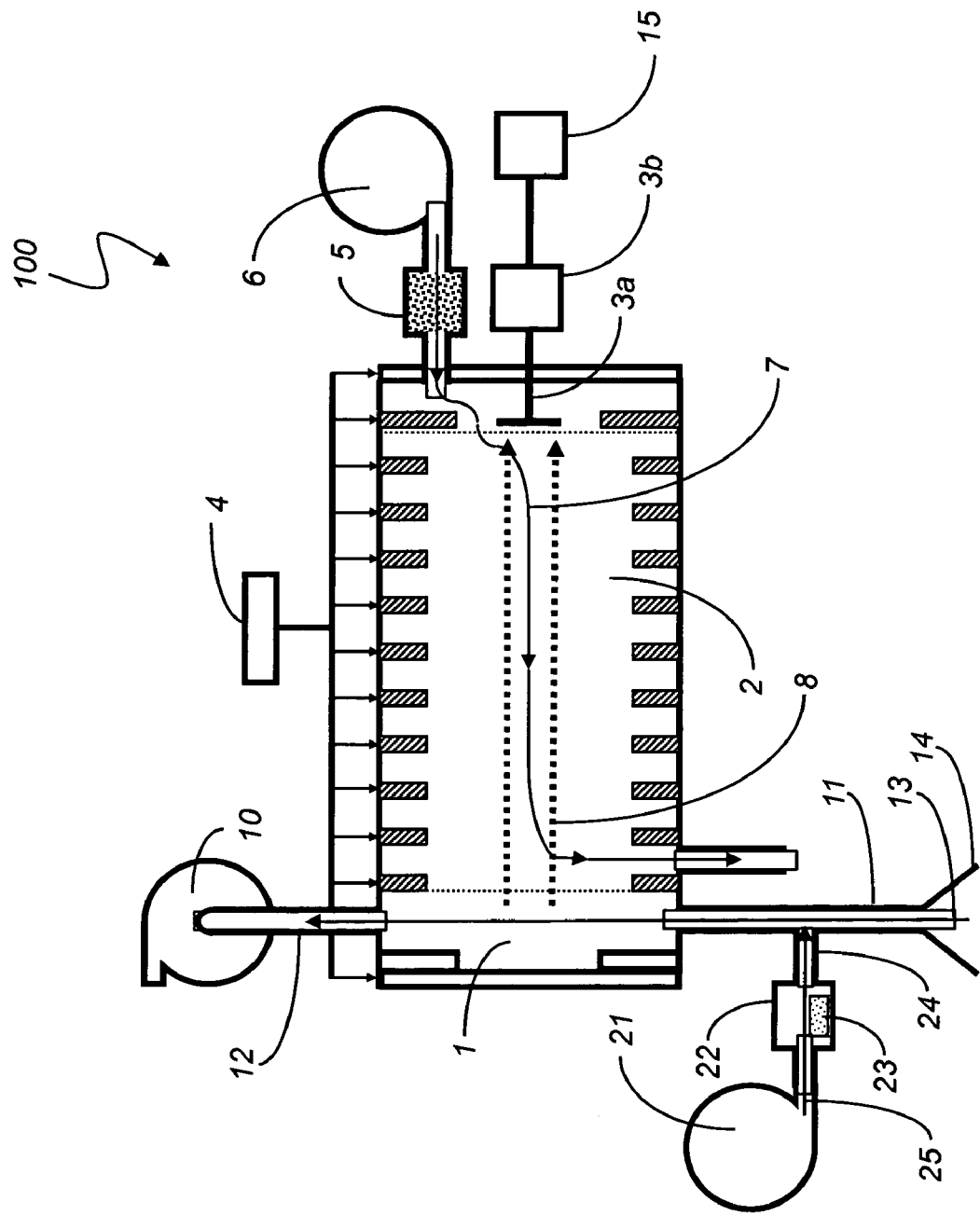
FIG. 1 is an example of an ion mobility spectrometer that may be used in connection with the system and method described herein.

Referring now to FIG. 1, shown is an example of an ion mobility spectrometer (IMS) 100 that may be used in connection with the system and method described herein. The IMS includes an ionization region 1 coupled to a drift region 2. At the end of the drift region 2 that is disposed opposite to the ionization region 1 is a charge collecting surface 3a that is coupled to a charge amplifier 3b. The drift region 2 has an inlet and an outlet for a drift gas 7, which is provided by pump 6 and is dried using a drying compound 5, such as a molecular sieve. The flow of drift gas 7 is towards the ionization region 1. An electric field generator 4 may provide an electric field to transport ions 8 between the ionization region 1 and the collecting surface 3. For example, the electric field generator 4 may include a voltage divider network.

The ionization region 1 may have a sample gas inlet tube 11 and a sample gas outlet tube 12. A pump 10 draws sample gas 13 from the sample gas inlet 14. An oven 22 is provided for a calibrant chemical 23 in order to heat the solid phase chemical to a temperature in the range of 40 degrees Celsius and the melting point of 5-nitrovanillin in order to provide sufficient vapor. A pump 21 provides a carrier gas 25 to direct the calibrant chemical gas into the sample gas inlet tube 11 together with sample gas 13.

The carrier gas and calibrant chemical gas 25 are transported to the ionization region 1, wherein the calibrant chemical gas is ionized. The ions 8 drift to the charge collecting surface 3a where the signal is amplified by the charge amplifier 3b. The actual drift time for this known calibrant chemical may then be employed to determine the expected drift times of target chemicals based on the ratio of the reduced mobility for the target chemical and calibrant chemical times the measured drift time, for example using a computer system 15 and/or other analysis unit, that may include software stored on a computer-readable medium, coupled to the charge amplifier 3b and/or otherwise coupled to the ion mobility spectrometer to receive information therefrom.

Figure 2:
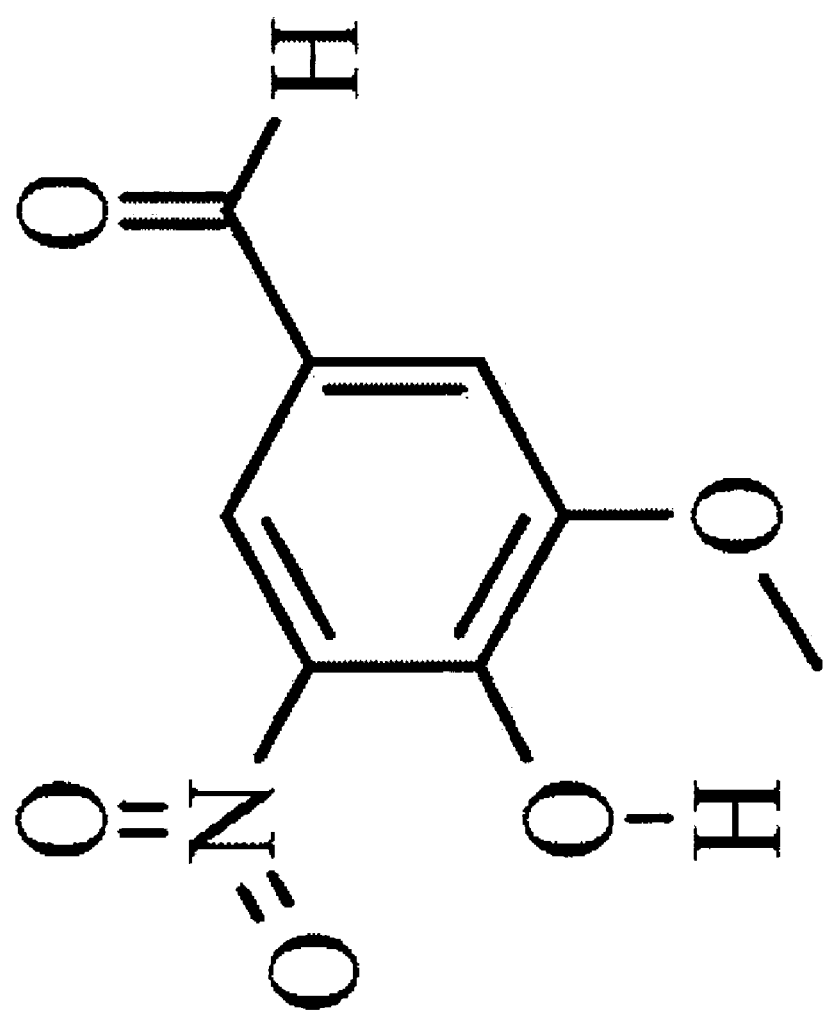
FIG. 2 is a depiction of the chemical structure of the 5-nitrovanillin molecule.

Referring now to FIG. 2, shown is a diagram of the molecule for the calibrant chemical 5-nitrovanillin. The IUPAC name is 4-hydroxy-3-methoxy-5-nitrobenzaldehyde. The CAS number is 6635-20-7. The chemical formula is $C_8H_7NO_5$.

Figure 3:
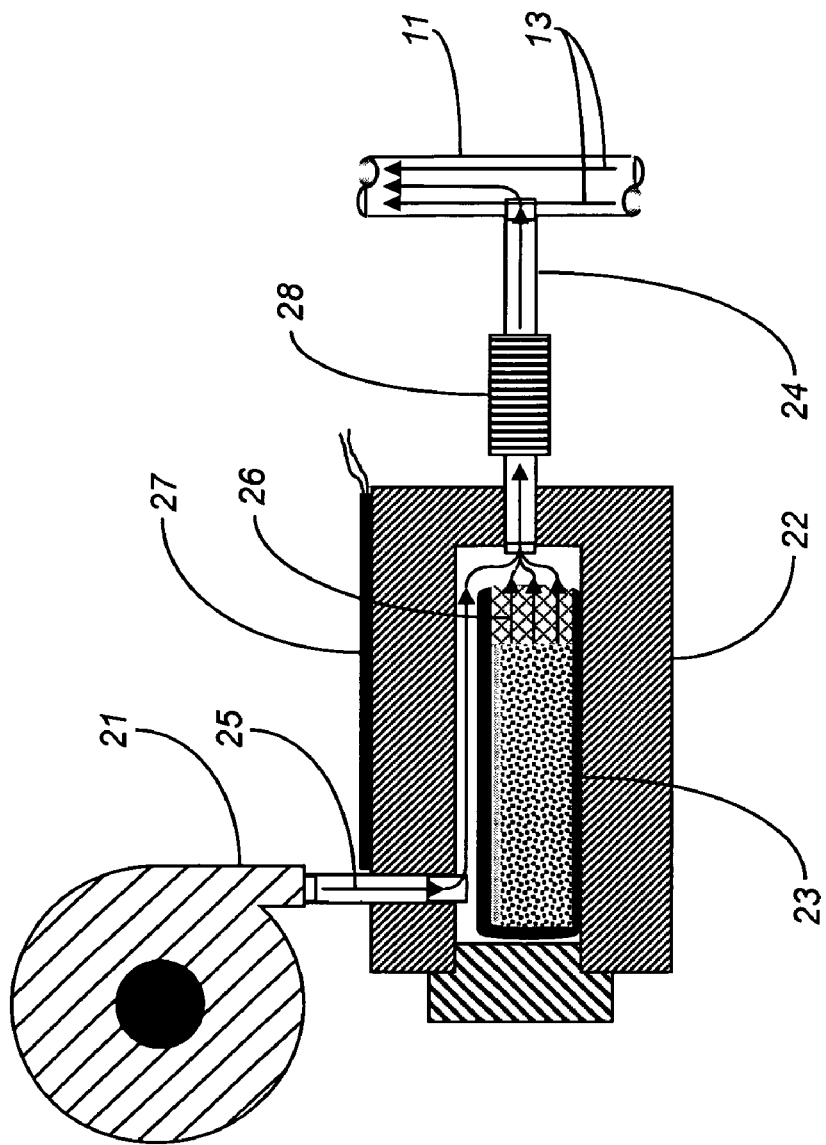
FIG. 3 is an example of a calibrant gas dispensing system that may be used in connection with the system and method described herein.

Referring now to FIG. 3, shown is an example of an embodiment of a dispensing system for the calibrant chemical that may be used in connection with the system and method described herein. The solid phase calibrant chemical is contained within the capsule 23. The capsule 23 is contained within a heated enclosure or oven 22 that is heated by electrical heating device 27. The oven 22 is heated to a temperature between 40 degrees Celsius and the melting point of 5-nitrovanillin to provide calibrant gas from the vapor pressure of the calibrant chemical. A pump 21 provides a carrier gas including either ambient air or dried air to produce a flow of carrier gas and calibrant chemical gas into a tube 24 that is in pneumatic communication with gas sampling tube 11. A valve 28, which may include at least one of a relief valve and an electrically operated shutoff valve, is used to prevent calibrant chemical gas from entering the gas sampling tube 11 between calibration cycles of the ion mobility spectrometer. The combined carrier gas and chemical calibrant gas 25 is further combined with a gas sample of ambient air in the gas sampling tube and transported to the ionization region of the ion mobility spectrometer.

Figure 4:
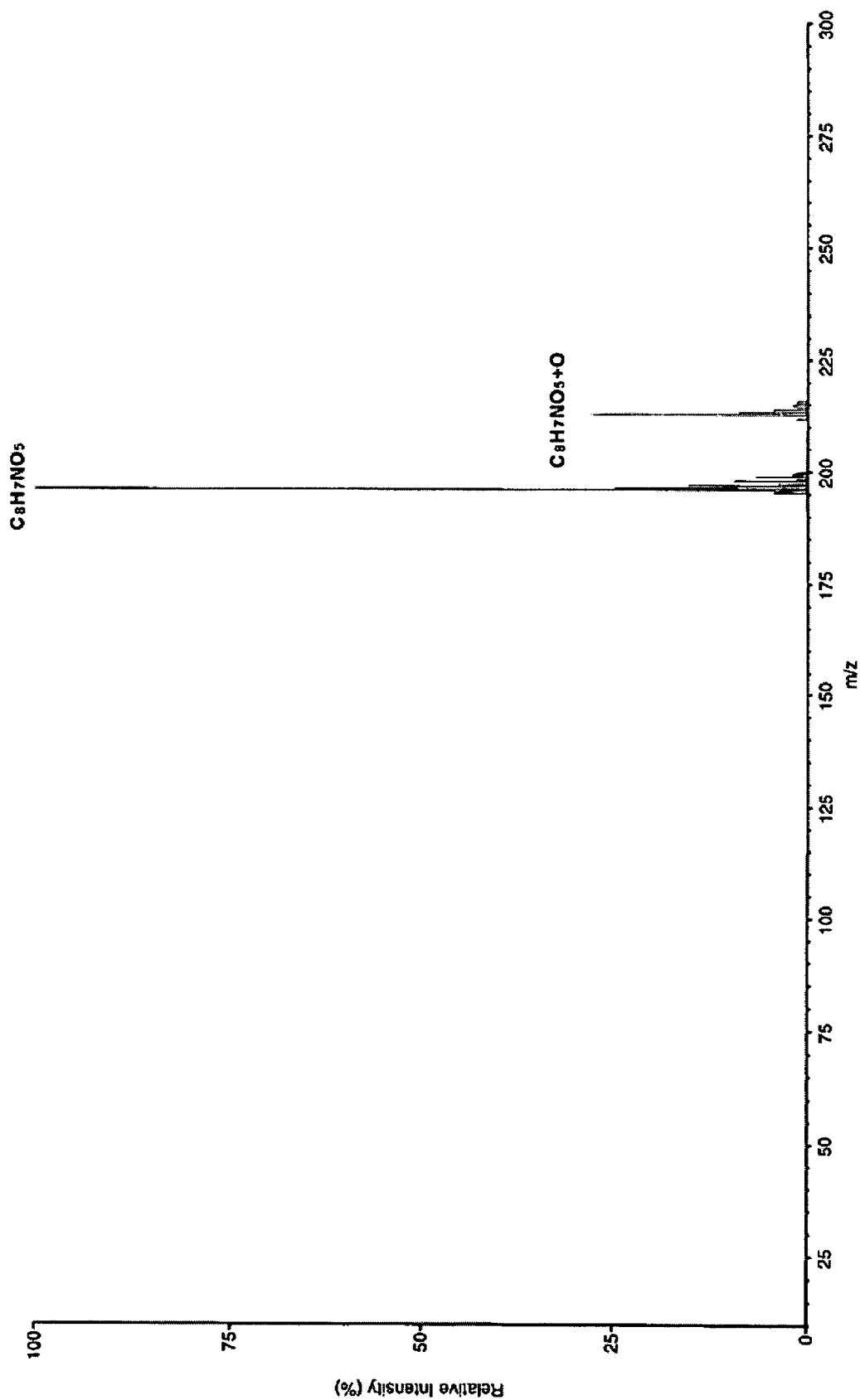
FIG. 4 is a set of data showing the mass spectrum of chemical species produced following negative ionization of the 5-nitrovanillin calibrant molecule.

Referring now to FIG. 4, shown is an example of data that shows the mass spectrum of molecular species produced as a result of negative ionization of the 5-nitrovanillin molecule. The species observed include 5-nitrovanillin, mass 197, and closely related species with up to 3 hydrogen atoms either added or removed. In an ion mobility spectrometer all of these species may appear as a single substance with substantially the same mobility as that of 5-nitrovanillin.

Figure 5:
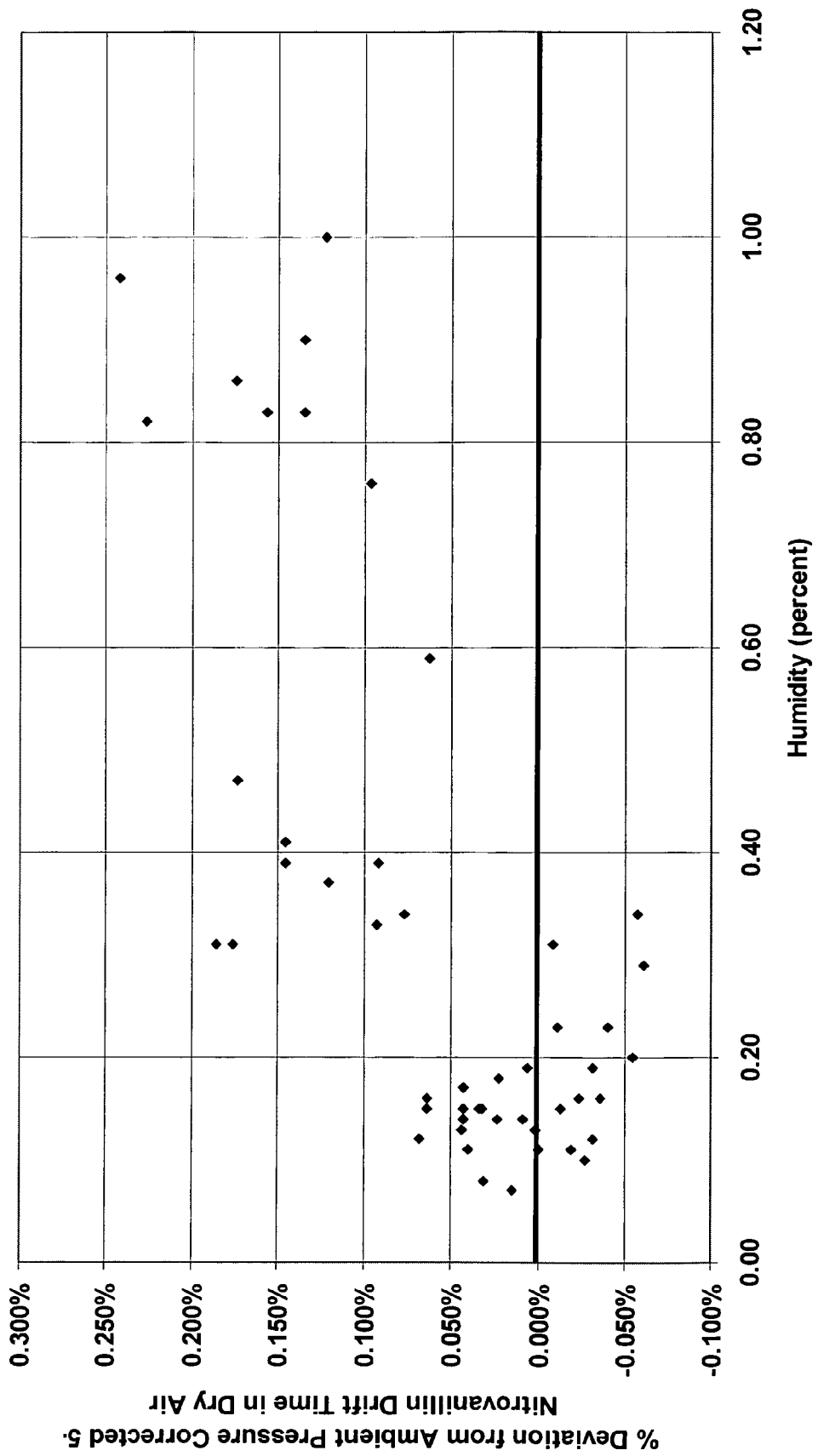
FIG. 5 is a set of data showing humidity within the ion mobility spectrometer and the percentage deviation of the observed ambient pressure-corrected drift time of the 5-nitrovanillin calibrant molecule from the observed ambient pressure-corrected drift time of the 5-nitrovanillin molecule under dry air conditions when measured in accordance with the system and method described herein.

Referring now to FIG. 5, shown is an example of data that shows the sensitivity of the drift time of 5-nitrovanillin to the level of humidity within the ion mobility spectrometer. It may be desirable for the change in drift time with humidity to be as little as possible. The figure shows the change in the deviation of the ambient pressure corrected drift time at the indicated humidity percentage from the ambient pressure corrected drift time of 5-nitrovanillin under dry air conditions. Ion mobility spectrometers may maintain air with a humidity level well below 1 percent to avoid changes in the drift times of target chemicals. In the case of 5-nitrovanillin, the change in drift time under these conditions is only about 0.18%.

Figure 6:
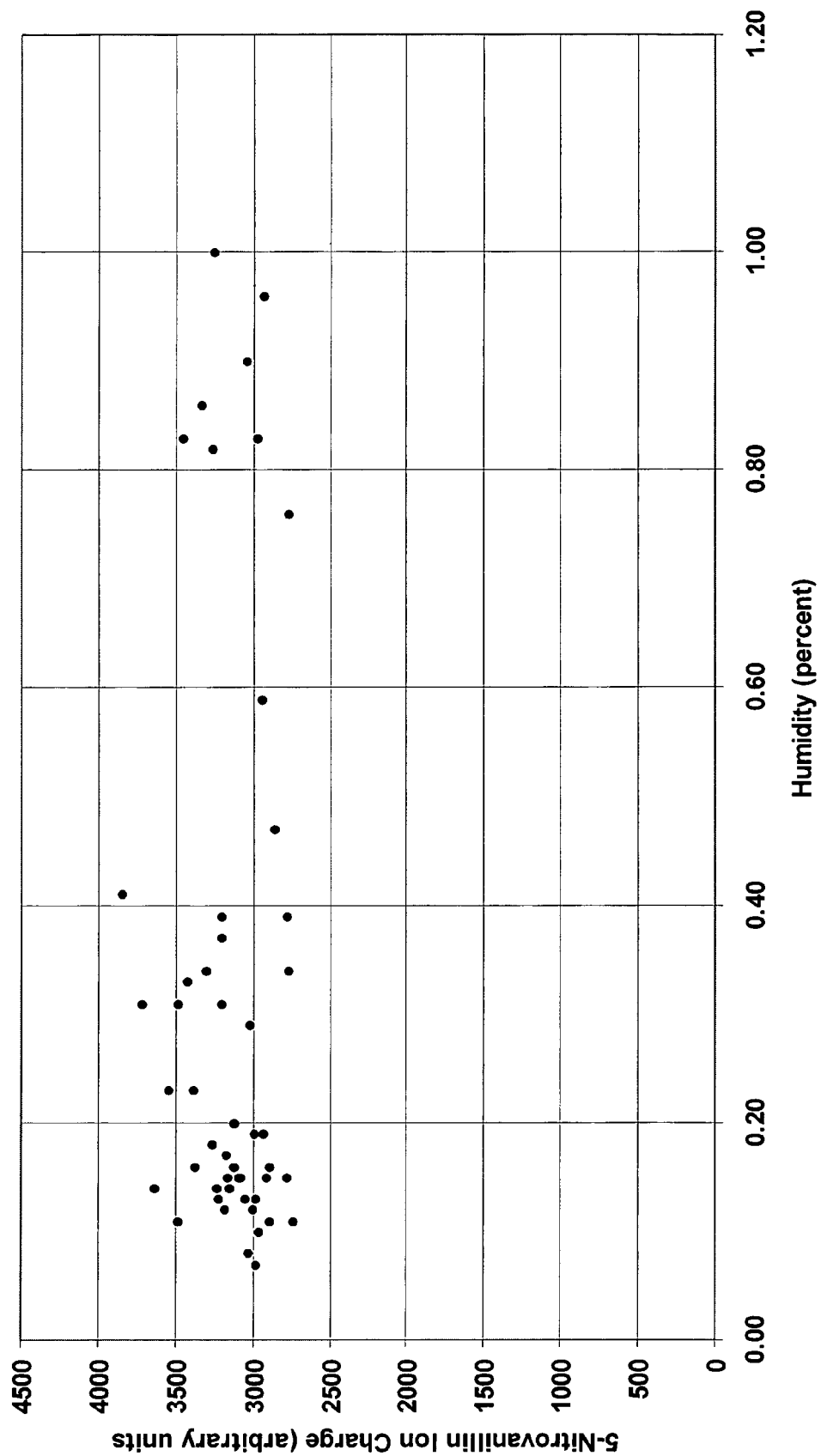
FIG. 6 is a set of data showing the ion charge amplitude for a family of gas samples of 5-nitrovanillin at various levels of humidity within the ion mobility spectrometer and measured in accordance with the system and method described herein.

Referring now to FIG. 6, shown is an example of data where the sensitivity of the negative charge amplitude of 5-nitrovanillin to the level of humidity within the ion mobility spectrometer. It may be desirable for the change in charge amplitude with humidity of the 5-nitrovanillin to be as little as possible.

Figure 7:
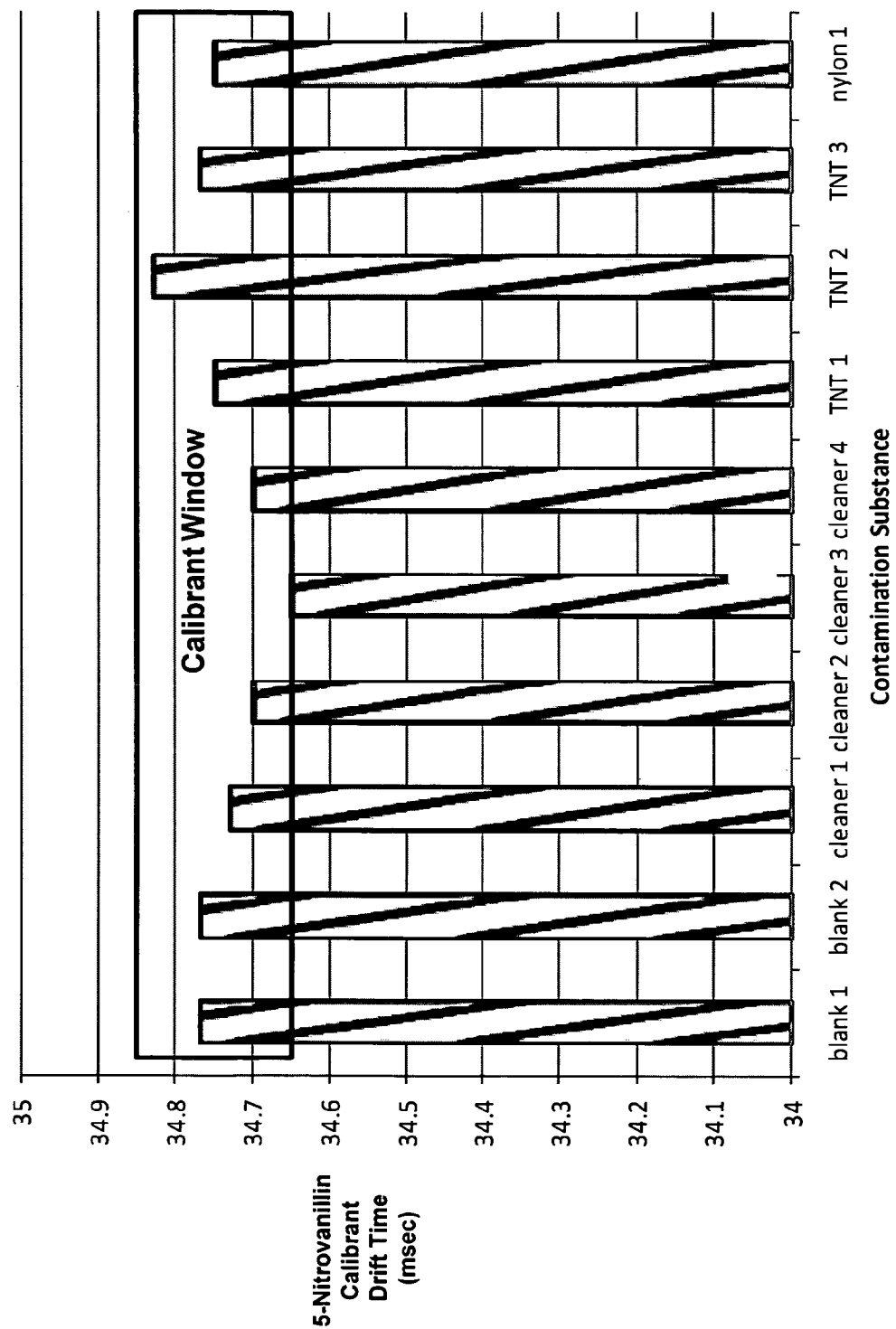
FIG. 7 is a set of data showing that the drift time for 5-nitrovanillin is largely independent of the indicated list of contaminating chemicals.
Figure 8:
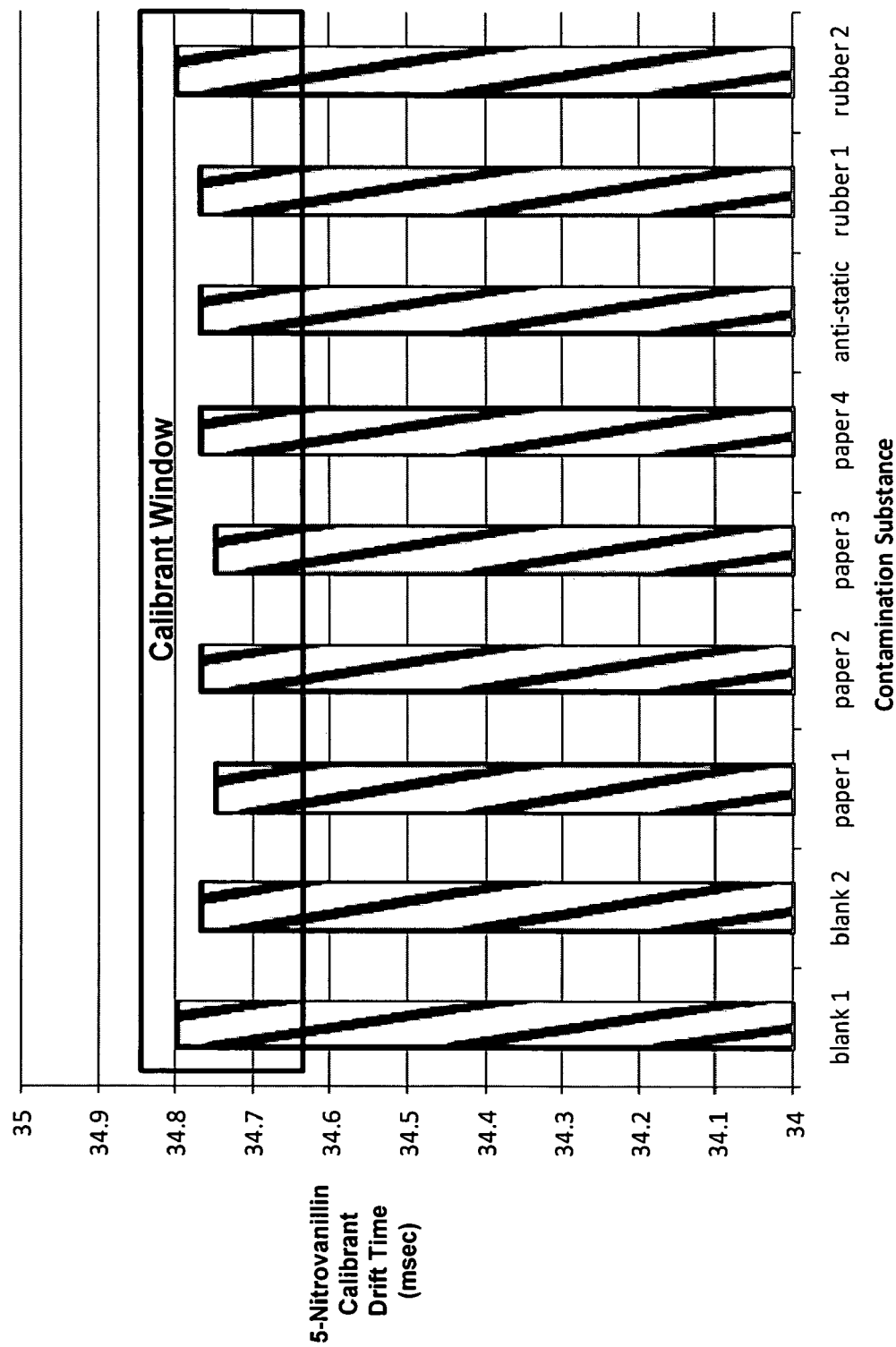
FIG. 8 is a set of data showing that the drift time for 5-nitrovanillin is largely independent of the indicated list of contaminating chemicals.

Referring now to FIGS. 7 and 8, shown are examples of data that show the variation in drift time of 5-nitrovanillin in the presence of a variety of indicated chemical contaminant species. The horizontal bands in the figures show the typical expected range of values (the "window") for the drift time of 5-nitrovanillin without the presence of contaminant species. It is desirable for the change in drift time of the 5-nitrovanillin in the presence of contaminant species to be as little as possible. In many cases the test article that was emitting the contaminant species was repeatedly presented to the sampling gas input tube to test for the effect of accumulated buildup of contamination. These data demonstrate that for these tested species, the drift time of 5-nitrovanillin is little affected.

Figure 9:
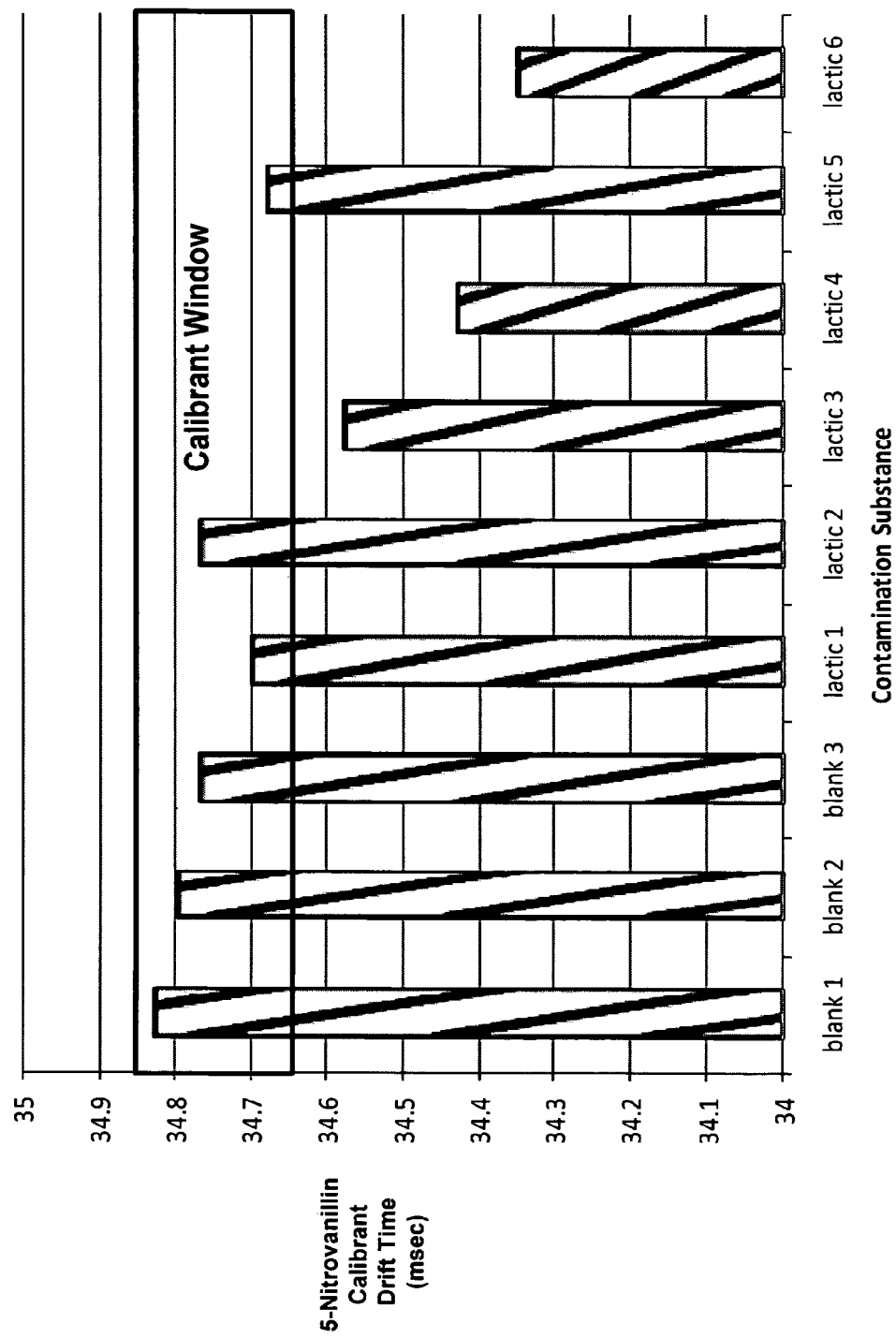
FIG. 9 is a set of data showing that the drift time for 5-nitrovanillin is dependent on the presence of contaminating lactic acid and its oxide derivatives.

Referring now to FIG. 9, shown is an example of data that shows the effect of the presence of lactic acid or its oxide derivatives on the drift time of 5-nitrovanillin. In this example it may be seen that the drift time of the 5-nitrovanillin is significantly affected by the lactic acid or its oxide derivatives. This is an indication that the instrument software, and/or other analytical unit, may consider the presence of lactic acid or its oxide derivatives. One option is to make a drift time correction based on the observed concentration of lactic acid or its oxide derivatives. A second option is not to accept the drift time of 5-nitrovanillin as measured and periodically repeat the measurement until the concentration of lactic acid or its oxide derivatives has decreased below a predetermined level. A third option is to increase the concentration of 5-nitrovanillin consistent with the observed concentration of the lactic acid or its derivatives in order to decrease the error in drift time.

The system and method described herein may incorporate other features, such as features described in commonly assigned copending and/or issued U.S. patents and/or patent applications incorporated by reference herein, including: U.S. provisional patent application No. 60/708,017 filed on Aug. 12, 2005; U.S. patent application Ser. No. 10/890,820 filed on Jul. 14, 2004; U.S. Pat. No. 6,828,795; U.S. patent application Ser. No. 10/295,039 filed on Nov. 14, 2002; U.S. Pat. No. 6,861,646; U.S. provisional application No. 60/357,394, filed Feb. 15, 2002; U.S. provisional application No. 60/357,618, filed Feb. 15, 2002; U.S. provisional application No. 60/363,485, filed Mar. 12, 2002; U.S. patent application Ser. No. 10/853,563, filed May 25, 2004; U.S. provisional patent Application No. 60/473,649, filed May 29, 2003; U.S. patent application Ser. No. 10/818,434 filed on Apr. 5, 2004; U.S. Pat. No. 6,861,646; U.S. patent application Ser. No. 10/295,039 filed on Nov. 14, 2002; U.S. Pat. No. 6,828,795; U.S. Pat. No. 6,888,128; U.S. Provisional Application No. 60/357,394, filed Feb. 15, 2002; U.S. Provisional Application No. 60/357,618, filed Feb. 15, 2002; U.S. Provisional Application No. 60/363,485, filed Mar. 12, 2002, all of which are incorporated herein by reference.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for calibrating drift time for an ion mobility spectrometer that is open to the atmosphere, the ion mobility spectrometer including a gas ionization region with a sample gas inlet tube and sample gas outlet tube open to the atmosphere, a drift region with an inlet and outlet for a drift gas flow and pneumatically coupled to the ionization region, a charge collecting surface at the end of the drift region opposite the ionization region, and an electric field generator for providing an electric field between said ionization region and said charge collecting surface in order to transport ions in between, the method comprising:
   heating a solid phase sample of a calibrant chemical to produce a calibrant gas using a temperature controlled oven in pneumatic communication with said ionization region, wherein said calibrant chemical includes 5-nitrovanillin, also known as 4-hydroxy-3-methoxy-5-nitrobenzaldehyde, CAS number 6635-20-7;
   determining the drift time of ions of said calibrant chemical through said ion mobility spectrometer; and
   determining the expected drift time of a target chemical using a pre-determined ratio of the reduced mobilities of said target chemical and said calibrant chemical.

2. The method of claim 1, wherein said temperature-controlled oven is operated at a temperature between 40 degrees Celsius and the melting point of 5-nitrovanillin.

3. The method of claim 1, wherein said calibrant gas is injected into said ionization region using a carrier gas including at least one of pressurized ambient air and pressurized dry air.

4. The method of claim 1, wherein said solid phase sample of calibrant chemical has a purity greater than 90%.

5. The method of claim 1, wherein said drift time is determined based on the difference in the ion charge arrival time at said charge collecting surface and the time of either a pulsed ionization event or the opening of an electronic ion gate.

6. The method of claim 1, wherein said drift time is discarded if an amplitude of calibrant chemical ion charge is less than 1% of a possible full scale detection amplitude or greater than 30% of the possible full scale detection amplitude.

7. The method of claim 1, wherein said drift time is discarded if an ion charge peak corresponding to lactic acid or oxide derivatives thereof appears in the spectrum of drift time with an amplitude greater than half the amplitude of the ion charge peak corresponding to 5-nitrovanillin.

8. A system for calibrating drift time, comprising:
   an ion mobility spectrometer that is open to the atmosphere, the ion mobility spectrometer including a gas ionization region with a sample gas inlet tube and sample gas outlet tube open to the atmosphere, a drift region with an inlet and outlet for a drift gas flow and pneumatically coupled to the ionization region, a charge collecting surface at the end of the drift region opposite the ionization region, and an electric field generator for providing an electric field between said ionization region and said charge collecting surface in order to transport ions in between;
   a temperature controlled oven in pneumatic communication with said ionization region that heats a solid phase sample of a calibrant chemical to produce a calibrant gas, wherein said calibrant chemical includes 5-nitrovanillin, also known as 4-hydroxy-3-methoxy-5-nitrobenzaldehyde, CAS number 6635-20-7; and
   an analysis unit that determines the drift time of said calibrant chemical through said ion mobility spectrometer and determines the expected drift time of a target chemical using pre-determined ratio of the reduced mobilities of said target chemical and said calibrant chemical.

9. The system of claim 8, wherein said temperature-controlled oven is operated at a temperature between 40 degrees Celsius and the melting point of 5-nitrovanillin.

10. The system of claim 8, wherein said calibrant gas is injected into said ionization region using a carrier gas including at least one of pressurized ambient air and pressurized dry air.

11. The system of claim 8, wherein said solid phase sample of calibrant chemical has a purity greater than 90%.

12. The system of claim 8, wherein said drift time is determined based on the difference in the ion charge arrival time at said charge collecting surface and the time of either a pulsed ionization event or the opening of an electronic ion gate.

13. The system of claim 9, wherein said drift time is discarded if the amplitude of calibrant chemical ion charge is less than 1% of the possible full scale detection amplitude or greater than 30% of the possible full scale detection amplitude.

14. The system of claim 9, wherein said drift time is discarded if an ion charge peak corresponding to lactic acid or oxide derivatives thereof appears in the spectrum of drift time with an amplitude greater than half the amplitude of the ion charge peak corresponding to 5-nitrovanillin.

15. A method for calibrating drift time for an ion mobility spectrometer that is open to the atmosphere, comprising:
   heating a solid phase sample of a calibrant chemical to produce a calibrant gas using a temperature controlled oven in pneumatic communication with an ionization region of the ion mobility spectrometer, wherein said calibrant chemical includes 5-nitrovanillin;
   determining the drift time of said calibrant chemical through said ion mobility spectrometer; and
   determining the expected drift time of a target chemical using a pre-determined ratio of the reduced mobilities of said target chemical and said calibrant chemical.

16. The method of claim 15, wherein said temperature-controlled oven is operated at a temperature between 40 degrees Celsius and the melting point of 5-nitrovanillin.

17. The method of claim 15, wherein said calibrant gas is injected into an ionization region of the ion mobility spectrometer using a carrier gas including at least one of pressurized ambient air and pressurized dry air.

18. The method of claim 15, wherein said solid phase sample of calibrant chemical has a purity greater than 90%.

19. The method of claim 15, wherein said drift time is determined based on the difference in the ion charge arrival time at a charge collecting surface of the ion mobility spectrometer and the time of either a pulsed ionization event or the opening of an electronic ion gate.

20. The method of claim 15, wherein said drift time is discarded if an amplitude of calibrant chemical ion charge is less than 1% of a possible full scale detection amplitude or greater than 30% of the possible full scale detection amplitude.

21. The method of claim 15, wherein said drift time is discarded if an ion charge peak corresponding to lactic acid or oxide derivatives thereof appears in the spectrum of drift time with an amplitude greater than half the amplitude of the ion charge peak corresponding to 5-nitrovanillin.

* * * * *